United States Patent [19]

Kanaya et al.

[11] Patent Number: 5,814,621
[45] Date of Patent: Sep. 29, 1998

[54] DRUG COMPOSITION AND PROCESS FOR PREPARING THE SAME

[75] Inventors: Yoshio Kanaya; Hiroshi Yuasa; Daisaku Oguni, all of Tokyo, Japan

[73] Assignee: Seikagaku Kogyo Kabushiki Kaisha, Tokyo, Japan

[21] Appl. No.: 591,899

[22] Filed: Jan. 25, 1996

Related U.S. Application Data

[63] Continuation of Ser. No. 185,712, Jan. 24, 1994, abandoned.

[30] Foreign Application Priority Data

Jan. 25, 1993 [JP] Japan .................................. 5-028547

[51] Int. Cl.$^6$ ..................... A61K 31/715; A61K 31/725; A61K 31/73
[52] U.S. Cl. ................................. 514/54; 514/55; 514/56; 536/20; 536/21; 536/123; 536/123.1; 424/418
[58] Field of Search ................................. 514/42, 54, 56, 514/951, 964, 55; 536/18.7, 21, 123, 123.1, 20; 424/418, 461, 479, 488, 493, 499

[56] References Cited

U.S. PATENT DOCUMENTS

| | | | |
|---|---|---|---|
| 3,887,703 | 6/1975 | Manoussos et al. ........................ | 424/95 |
| 4,533,549 | 8/1985 | Lasker ........................................ | 514/56 |
| 4,686,288 | 8/1987 | Lormeau et al. .......................... | 536/21 |
| 4,925,677 | 5/1990 | Feijen ....................................... | 424/484 |
| 4,937,270 | 6/1990 | Hamilton et al. ......................... | 514/777 |
| 5,143,724 | 9/1992 | Leshchiner et al. .................. | 424/78.08 |
| 5,185,152 | 2/1993 | Peyman ..................................... | 424/427 |
| 5,246,698 | 9/1993 | Leshchiner et al. .................. | 424/78.08 |

FOREIGN PATENT DOCUMENTS

| | | |
|---|---|---|
| 0 224 987 | 6/1987 | European Pat. Off. . |
| 0 263 490 | 4/1988 | European Pat. Off. . |
| 640647 | 3/1995 | European Pat. Off. . |

OTHER PUBLICATIONS

Brown et al. *International Journal of Tissue Reactions*, vol. 17(4): 133–140, (1995) Absract only.
Miura et al. *Front. New Horiz. Amino Acid Res., Proc. Bienn. Int. Conf., 1st,* pp. 385–389, (1992) Abstract only.
Gurny et al. *J. Controlled Release*, vol. 6:367–373, (1987) Abstract only.

*Primary Examiner*—John Kight
*Assistant Examiner*—Howard C. Lee
*Attorney, Agent, or Firm*—Testa, Hurwitz & Thibeault, LLP

[57] ABSTRACT

A drug composition comprising a mucopolysaccharide (also referred in the art as a glycosaminoglycan) and a drug which is scarcely soluble in water but soluble in a water-miscible organic solvent, wherein fine crystals or fine particles of the drug is attached on or between the particles of a mucopolysaccharide, and a process for preparing the same. The drug composition of the present invention exhibits greatly improved solubility and a dissolution rate of the drug, and thus greatly improve the drug's bioavailability.

15 Claims, 4 Drawing Sheets

DRUG COMPOSITION AND PROCESS FOR PREPARING THE SAME

This is a continuation of application Ser. No. 08/185,712 filed on Jan. 24, 1994, now abandoned.

BACKGROUND OF THE INVENTION

1. Field of the Invention

The present invention relates to a drug composition comprising a scarcely soluble drug carried on a mucopolysaccharide (also referred in the art as a glycosaminoglycan) as a carrier, and to a process for the preparation of the drug composition. According to the drug composition of the present invention, drugs which are difficult to be dissolved can be provided with improved dissolution capability.

2. Description of the Background Art

Drugs orally administered are generally disintegrated, dispersed, and dissolved in the intestinal tract. Only drugs thus dissolved in the intestinal tract can be absorbed by the subject's body. The dissolution capability or the solubility of a drug is therefore an important parameter which regulates the period of time before the drug exhibits its effect and the bioavailability.

The drugs called scarcely soluble drugs are extremely difficult to dissolve in water. Because the dissolution rate of a drug is regulative of absorption by the intestinal tract, these scarcely soluble drugs are absorbed only very slowly after they are orally administered. The absolute absorptivity of many of these drugs is limited. Therefore, in an effort to make these drugs easily soluble in water they are converted to acid salts, base salts, or water-soluble prodrugs. As another effort to make them more soluble, a solubilizer such as a surfactant is added or the drug is included in cyclodextrin or the like when the drug is formulated. Furthermore, a raw powder of the drug is ground into fine powder or made non-crystalline.

Because these techniques are only effective for specific drugs, each must be applied to limited specific drugs. They are not the techniques which are applicable to all drugs. In particular, it is difficult to improve the rate of absorption of these scarcely soluble drugs, even though the absolute absorptivity (the total amount absorbed) has been improved to some extent.

In actual pharmacological applications, there are many scarcely soluble drugs which are required to promptly exhibit their effects after administration. Drugs for oral administration possessing not only abundant absorptivity, but also a high rate of absorption are therefore desired.

In view of this situation, the use of various high molecular weight compounds for the improvement in the absorptivity of scarcely soluble drugs have been studied. For example, Japanese Patent Laid-open (kokai) No. 26615/1982 describes a method of grinding a scarcely soluble drug together with high molecular weight gelatin or the like. This method, however, requires the addition of a great amount of gelatin in order to improve the absorptivity of scarcely soluble drugs. In addition, the method of preparation is limited to grinding of a mixture of the materials.

Japanese Patent Publication (kokoku) Nos. 28414/1988 and Japanese Patent Laid-open (kokai) 131434/1990 disclose a method for improving the rate of absorption and the absorptivity by formulating a scarcely soluble drug together with chitin or chitosan obtained from the shell of crab or shrimp, by the grinding of mixture method, the wet (kneading) method or the dry process and the like. In this method, the scarcely soluble drug must be ground by a grinder and must be classified to regulate the particle size. This requires a long period of time for the preparation, while consuming a great amount of energy. Beside this method, there is known a method in which arginic acid is added instead of chitin or chitosan (Japanese Patent Laid-open (kokai) No. 225422/1990), a method of grinding a scarcely soluble drug together with powder of $\beta$-1,4-glucan (Japanese Patent Publication (kokoku) Nos. 22138/1978, 29565/1979), kneading a scarcely soluble drug together with a water-soluble high molecular compound base material (Japanese Patent Laid-open (kokai) No. 63614/1986), and a method of having a scarcely soluble drug adsorbed in and carried on the surface of processed starch (Japanese Patent Laid-open (kokai) No. 101333/1988). All these methods have the same problems as mentioned above.

There have been no methods disclosed involving the use of a mucopolysaccharide in order to improve the dissolution capability of scarcely soluble drugs. There has been also no prior art concerning a technique in which fine crystals or fine particles of a scarcely soluble drug are attached by deposition on or between the particles of a mucopolysaccharide.

The present inventors have undertaken extensive investigations concerning the effects of the addition of a mucopolysaccharide on the improvement of the dissolution capability of scarcely soluble drugs, and found that the capability of and the rate of dissolution of a drug can be improved if the mucopolysaccharide and the drug dissolved in a water-miscible organic solvent such as a polar solvent or a solvent having comparatively high polarity, are brought into contact with each other to form a drug composition having a specific structure in which fine crystals or fine particles of the drug are attached by deposition on or between the particles of the mucopolysaccharide. This finding has led to the completion of the present invention.

SUMMARY OF THE INVENTION

Accordingly, an object of the present invention is to provide a composition of a scarcely soluble drug with improved water solubility and dissolution rate.

Another object of the present invention is to provide a granular drug composition in which fine crystals or fine particles of a drug, which is scarcely soluble in water but soluble in a water-miscible organic solvent are, attached on or between the particles of a mucopolysaccharide.

A further object of the present invention is to provide a process for the preparation of a composition of a scarcely soluble drug with improved water solubility and dissolution rate by a simple method in which a solution of the scarcely soluble drug is used.

The above object can be achieved according to the present invention by a process which comprises, preparing an aqueous solution of a mucopolysaccharide or a salt thereof and a solution of a drug, which is scarcely soluble in water but soluble in a water-miscible organic solvent, dissolved in the water-miscible organic solvent; and subjecting the two solutions to contact with each other, thus producing precipitate particles (hereinafter called the first process).

The above object can be further achieved according to the present invention by a process which comprises, preparing an aqueous solution of a mucopolysaccharide or a salt thereof; subjecting this solution to contact with a water-miscible organic solvent, thus precipitating particles of the mucopolysaccharide; and subjecting the particles of the mucopolysaccharide to contact with a solution of a drug, which is scarcely soluble in water but soluble in a water-miscible organic solvent, dissolved in the water-miscible organic solvent, thus subjecting fine crystals or fine particles of the drug to attachment on or between the particles of the mucopolysaccharide (hereinafter called the second process).

Other and further objects, features and advantages of the present invention will appear more fully from the following description.

DETAILED DESCRIPTION OF THE INVENTION AND PREFERRED EMBODIMENTS

Figure 1:
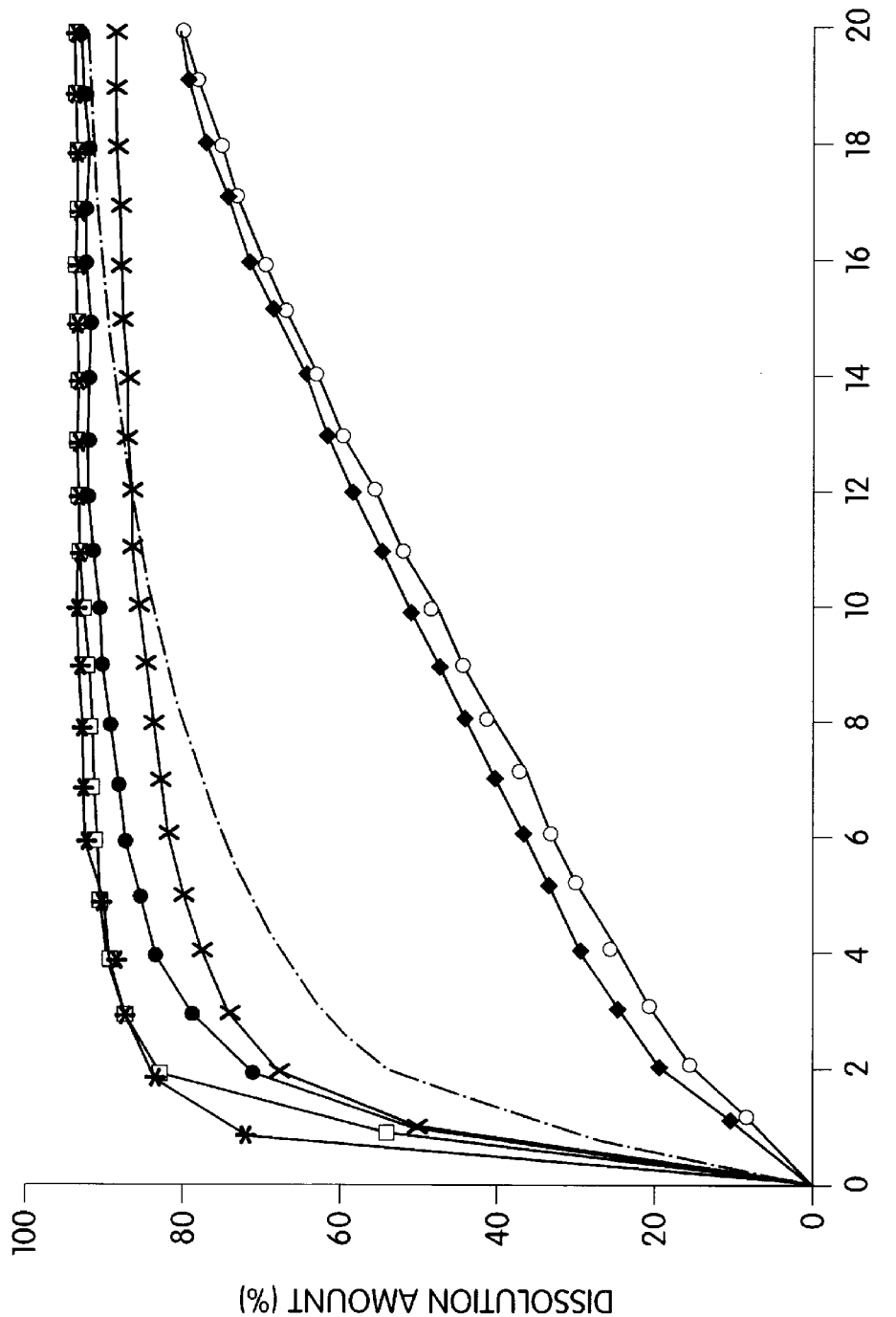
FIG. 1 shows dissolution rates of a phenacetin powder and the composition of the present invention over time obtained in a Test Example, in which the curve connected by open circles indicates the dissolution rate of phenacetin alone; the broken line, the dissolution rate of the composition of the present invention obtained when the solution was stirred at 200 rpm; the curve connected by crosses, at 250 rpm; the curve connected by solid circles, at 300 rpm; the curve connected by open squares, at 400 rpm; the curve connected by asterisks, at 500 rpm; and the curve connected by solid squares, the dissolution rate of an 8:2 phenacetin-chondroitin sulfate mixture.

Mucopolysaccharides used in the present invention include chondroitin sulfate, chondroitin, hyaluronic acid, dermatan sulfate, heparin, heparan sulfate, kerato sulfate, keratan polysulfate, and a derivative of any of said compounds (acylated compounds, sulfated compounds, deacylated compounds, desulfated compounds, and the like). Either one kind of mucopolysaccharide or two or more kinds of these mucopolysaccharides as a mixture can be used in the present invention. They are preferably used as a salt of alkali metal (sodium, potassium, etc.), a salt of alkaline earth metal (magnesium, etc.), or a salt of tertiary amine (triethylamine, tributylamine, pyridine, etc.). There are no restrictions as to the source and the method of preparation of these mucopolysaccharides, including those extracted from living bodies such as cartilage, crista gelli, or navel string; those produced by fermentation; and those prepared or modified by an enzyme method or a chemical synthetic method. There are no limitations also to the molecular weight of the mucopolysaccharides. In the case of chondroitin sulfate or its salt, the weight average molecular weight may be in the range of $5 \times 10^3$ to $6 \times 10^4$ Dalton; and in the case of hyaluronic acid or its salt, the weight average molecular weight may be in the range of $5 \times 10^4$ to $2 \times 10^6$ Dalton. As aqueous solutions of the mucopolysaccharide or its salt, those obtained by dissolving the mucopolysaccharide or the salt thereof in neutral or alkaline water are preferred.

The scarcely soluble drugs useful in the present invention are drugs which are scarcely soluble in water but dissolved in a water-miscible organic solvent. Those possessing this characteristic are given as examples of the drugs used in the present invention. These drugs typically have an insufficient absorption rate and thus exhibit poor absorptivity (bioavailability).

The following drugs are given as examples.

(a) Hypnotics calmative

Nitrazepam, triazolam, phenobarbital, and amibarbital.

(b) Antiepileptics

Phenytoin, metharbital, primidone, clonazepam, carbamazepine, valproic acid and the like.

(c) Analgesic antipyretics (antiinflammatory)

Flurbiprofen, mefenamic acid, ketoprofen, ibuprofen, indomethacin, diclofenac acid, phenacetin, oxyphenbutazone, phenylbutazone, sulpyrine, pentazocine, piroxicam and the like.

(d) Antidizziness drugs

Meclizine hydrochloride, dimenhydrinate and the like.

(e) Psychotropic drugs

Haloperidol, meprobamate, chlordiazepoxide, diazepam, oxazepam, sulpiride and the like.

(f) Antispastics

Papaverine, atropine, etomidoline and the like.

(g) Cardiacs

Digoxin, digitoxin, methyldigoxin, ubidecarenone and the like.

(h) Antiarrhythmic agents

Pindrol, ajmaline, disopyramide and the like.

(i) Diuretics

Hydrochlorothiazide, spironolactone, triamterene, furosemide, bumetanide and the like.

(j) Antihypertensive agents

Reserpine, dihydroergotoxine mesylate, prazosin hydrochloride, metoprolol, propranolol, atenolol and the like.

(k) Coronary vasodilators

Nitroglycerin, isosorbide dinitrate, diltiazem, nifedipine, dipyridamole and the like.

(l) Antitussive drugs

Noscapine, salbutamol, procaterol, tulobuterol, tranilast, ketotifen and the like.

(m) Ameliorants of cerebral circulation

Nicardipine pinpocetin and the like.

(n) Antibiotics

Erythromycin, josamycin, chloramphenicol, tetracycline, rifampicin, griseofulvin and the like.

(o) Antihistamics

Diphenhydramine, promethazine, mequitazine and the like.

(p) Steroid drugs

Triamcinolone, dexamethasone, betamethasone, prednisolone, danazol, methyltestosterone, chlormadinone acetate and the like.

(q) Vitamins

Vitamin E, vitamin K, α-calcidol, phytonadione, nicotinic acid, dl-α-tocopherol, menatetrenone and the like.

(r) Others

Dicoumarol, cinnarizine, clofibrate, gefarnate, cimetidine, probenecid, mercaptopurine, methotrexate, ursodesoxycholic acid, dihydroergotamine mesylate and the like.

In view of dissolution capability of the raw materials, these scarcely soluble drugs are preferably ground by a grinder by a wet method or dry process and classified to have particle size of about 75–90 μm.

There are no specific limitations as to the water-miscible organic solvent which is used in the present invention in order to dissolve the scarcely soluble drugs and to precipitate mucopolysaccharide particles from the aqueous solution of mucopolysaccharide or a salt thereof, so long as such an water-miscible organic solvent can be applicable to the processes described hereinafter. Usually, a polarized organic solvent, a water-miscible organic solvent having comparatively high polarity, and a mixture of a non-polar solvent (benzene, toluene, ether, and the like) and a water-miscible organic solvent having comparatively high polarity are preferred. Especially, when the drug composition of the present invention is a drug composition for administration to human, ethanol, propanol, acetone, dimethylformamide (DMF), formic acid, acetic acid, and propionic acid are given as preferable examples.

The first process for the preparation of the drug composition of the present invention comprises preparing an aqueous solution of a mucopolysaccharide or a salt thereof and a solution of the scarcely soluble drug dissolved in the water-miscible organic solvent, and subjecting the two solutions to contact with each other for producing precipitate particles of the drug composition. It is desirable that the aqueous solution of the mucopolysaccharide or the salt thereof contain an inorganic salt such as sodium chloride, ammonium chloride, ammonium sulfate, or sodium sulfate. The addition of these inorganic salts brings about a salting-out effect, thereby making it easy to collect the target product. The contact of the two solutions can be carried out, for example, by dropping the solution of the scarcely soluble drug dissolved in the water-miscible organic solvent into the aqueous solution of the mucopolysaccharide, while stirring the latter solution at about 0°–60° C. The precipitate produced is then collected by a known solid-liquid separation means such as filtration, centrifuge, and decantation, and, optionally, dried to obtain the drug composition of the present invention. More preferably, the precipitate is washed with a saturated solution of the scarcely soluble drug dissolved in an organic solvent. This procedure can produce a drug composition with more uniform quality. After washing, the composition is dried at a temperature of about 40°–100° C. or by low temperature vacuum drying. Any drying method, such as hot air drying, low temperature vacuum drying, or the like, under the conditions which do not affect the quality of the drug, can be selected as appropriate.

The second process of the present invention comprises subjecting the aqueous solution of the mucopolysaccharide or a salt thereof to contact with a water-miscible organic solvent to precipitate particles of mucopolysaccharide and subjecting the particles of the mucopolysaccharide to contact with a solution of the scarcely soluble drug dissolved in the water-miscible organic solvent, to obtain the drug composition of the present invention. The contact of the two solutions can be carried out, for example, by dropping the water-miscible organic solvent into the solution of the mucopolysaccharide, while stirring the latter solution at about 0°–60° C. The precipitate produced is then, in the same manner as in the first process, collected by solid-liquid separation, washing with the saturated solution of the scarcely soluble drug dissolved in the water-miscible organic solvent, and, optionally, dried under the same conditions as in the first process, to obtain the drug composition of the present invention. In the same way as in the first process, it is desirable that the solution of the mucopolysaccharide or the salt thereof contain an inorganic salt such as sodium chloride.

In the first process, the concentration of the mucopolysaccharide or the salt thereof is preferably 0.1–25% by weight (hereinafter % by weight is referred to simply as %) and the concentration of the scarcely soluble drug in the organic solvent is preferably from 0.01% to the saturated concentration of the drug. In the second process, the concentration of the mucopolysaccharide or the salt thereof is, in the same way as in the first process, preferably 0.1–25%. The precipitated mucopolysaccharide particles are then subjected to contact with the organic solution of the scarcely soluble drug with a concentration of 0.01% to the saturated concentration of the drug. The use of the saturated solution of the drug in a water-miscible organic solvent is more preferable. When an inorganic salt such as sodium chloride is added in the first step, the preferable concentration of the inorganic salt is about 0.1 to 5M.

The amount of the drug in the composition of the present invention is 3–25%, and preferably about 7–8%.

The rate of stirring is normally about 100–6000 rpm, and, especially in the case of chondroitin sulfate, a preferable stirring rate is 200–500 rpm. The dropping rate of the organic solvent solution of the scarcely soluble drug in the first process is normally about 4–40 ml/min, and, especially in the case of chondroitin sulfate, a preferable dropping rate is 4.5–17.1 ml/min. The same range of dropping rate is applicable to the second process.

The drug composition of the present invention can be formulated by various methods and administered to humans. It can be used in the form of granules as are, or can be processed into tablets, capsules, troches, and the like.

Various known additives such as excipients, disintegrators, and lubricants can be incorporated in the drug composition of the present invention.

Illustrating an example of the methods by which the drug composition of the present invention is formulated, the granules prepared by the method mentioned above are dried and classified, blended with various additives, and made into tablets by the direct tablet method. The dry process or the grinding of mixture method are also applicable. For the purpose of masking or the like, the tablets or granules may be coated with a coating agent.

The tablets thus prepared exhibit greatly improved solubility and a dissolution rate of the scarcely soluble drug as compared with conventional drug compositions. They provide a drug with superior bioavailability.

According to the present invention, the combination of a mucopolysaccharide and a scarcely soluble drug for preparing a drug composition with a granular structure ensures an improved solubility and a dissolution rate of the scarcely soluble drug. Further, various types of formulations can be obtained from this granular drug composition by the conventional dry process, the grinding of mixture method, or the like.

Other features of the invention will become apparent in the following description of the exemplary embodiment which is given for illustration of the invention and is not intended to be limiting thereof.

EXAMPLE

Example 1

5.58 g of sodium chondroitin sulfate was slowly added to 40 ml of distilled water and stirred to dissolution. To the solution was added dropwise 300 ml of a 4.8% phenacetin solution in ethanol at a rate of 17.1 ml/min, while stirring the sodium chondroitin sulfate solution at 300 rpm and at a temperature of 35° C. The precipitate produced was collected by filtration, washed with a saturated ethanol solution of phenacetin, and dried at 50°–100° C. to obtain a drug composition containing phenacetin.

Phenacetin content: 12%

Dissolution rate: 90%

Average particle size: 700 μm

Example 2

8.77 g of sodium chloride was dissolved in 300 ml of distilled water. 3.35 g of sodium hyaluronate was slowly added to this solution and stirred to dissolution. To the solution was added a solution of 4.0 g of phenytoin in 400 ml of ethanol dropwise at a rate of 30 ml/min, while stirring the sodium hyaluronate solution at 5000 rpm. The precipitate produced was collected by filtration, washed with a saturated ethanol solution of phenytoin, and dried at 50°–100° C. to obtain 4.82 g of a drug composition containing phenytoin.

Phenytoin content: 7.69%

Example 3

9.64 g of sodium chondroitin sulfate was slowly added to 40 ml of distilled water and stirred to dissolution. To the solution was added 300 ml of an ethanol solution dropwise at a rate of 17.1 ml/min, while stirring the sodium chondroitin sulfate solution at 300 rpm and at a temperature of 35° C. The precipitate produced was collected by filtration, washed with a saturated ethanol solution of phenacetin, and dried at 50°–100° C. to obtain a drug composition containing phenacetin.

Test Example

The following tests were carried out to determine the dissolution rates of scarcely soluble drugs from drug compositions of the present invention.

(Test Method)

40 ml of an aqueous solution of 241.0 mg/ml sodium chondroitin sulfate was kept at 35° C. in a beaker, and while stirring this solution at 200–500 rpm, 300 ml of a solution of 4.8% phenacetin in ethanol was slowly added dropwise to produce precipitate. The precipitate was collected, washed twice with 100 ml of a saturated ethanol solution of phenacetin, and dried for 12 hours in a hot air thermostat at 40° C. to obtain Composition A of the present invention (the first process).

To 40 ml of the same aqueous solution of sodium chondroitin sulfate as above maintained at 35° C. was slowly added 300 ml ethanol dropwise while stirring under the same conditions as above. The precipitate produced was collected, washed twice with 100 ml of a saturated ethanol solution of phenacetin, and dried for 12 hours in a hot air thermostat at 40° C. to obtain Composition B of the present invention (the second process).

A phenacetin dissolution test was carried out using Compositions A and B in 900 ml of distilled water at a rotation of 100 rpm according to the second method in the Japanese Pharmacopeia, twelfth edition. The measurement of phenacetin was based on the degree of absorption at the maximum wavelength of 243 nm.

The dissolution effect of the composition prepared by the first process is shown in FIG. 1, in which is shown a remarkably high dissolution rate of phenacetin from the drug composition of the present invention at all stirring rate as compared with the control which is a phenacetin powder. Almost all phenacetin has dissolved out from the composition of the present invention within about 10 minutes. The dissolution test was also carried out using a mixture of sodium chondroitin sulfate and phenacetin. This mixture exhibited the similar dissolution effect as the phenacetin powder, showing no improvement in the dissolution of phenacetin.

Figure 2:
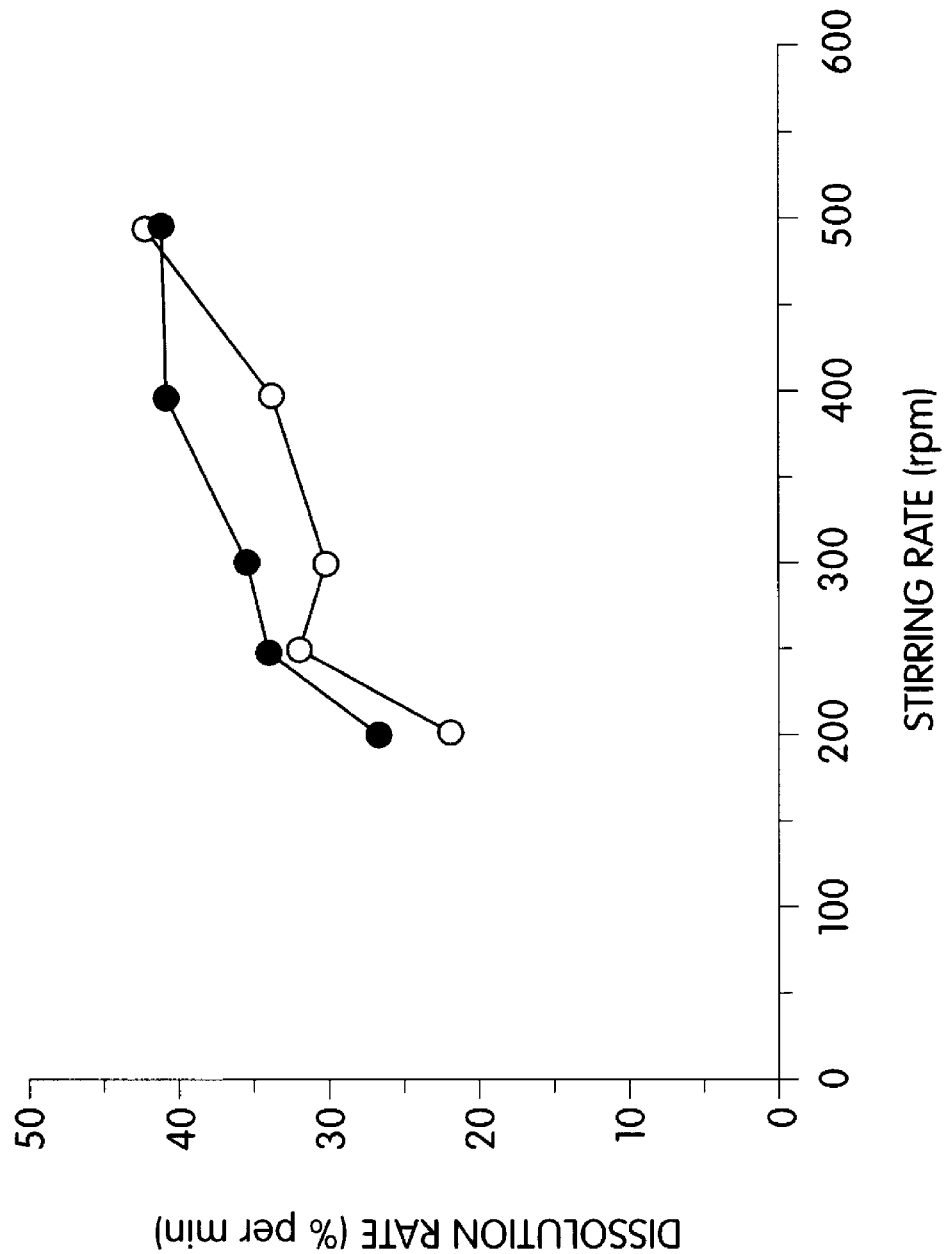
FIG. 2 shows the initial dissolution rates of phenacetin powder and of the compositions prepared by the first and second processes of the present invention over time obtained in a Test Example, in which the curve connected by open triangles indicates the dissolution rate of phenacetin alone; the curve connected by solid circles, the dissolution rate of the composition prepared by the first process of the present invention; and the curve connected by open circles, the dissolution rate of the composition prepared by the second process of the present invention.

FIG. 2 shows the results of a test, in which the initial dissolution rates of the compositions prepared by the first and second processes of the present invention and phenacetin powder were compared. The compositions of the present invention exhibited a remarkably high dissolution rate of phenacetin as compared with the phenacetin powder.

Figure 3:
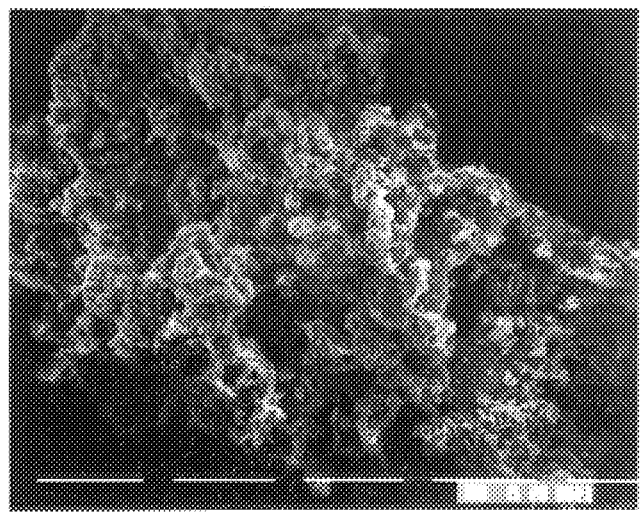
FIG. 3 is an electron microscopic photograph showing the structure of particles of the composition prepared in Example 1 of the present invention, at a magnification 200 times.
Figure 4:
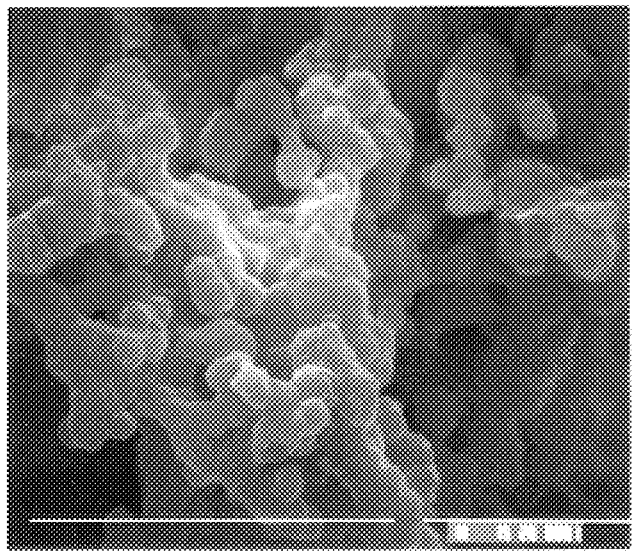
FIG. 4 is an electron microscopic photograph showing the structure of particles of the composition prepared in Example 1 of the present invention, at a magnification of 7500 times.

FIGS. 3 and 4 are electron microscopic photographs of the drug composition obtained in Example 1. The photographs show that the primary particles of sodium chondroitin sulfate are cross-linked and phenacetin is homogeneously present on and between the primary particles.

Figure 5:
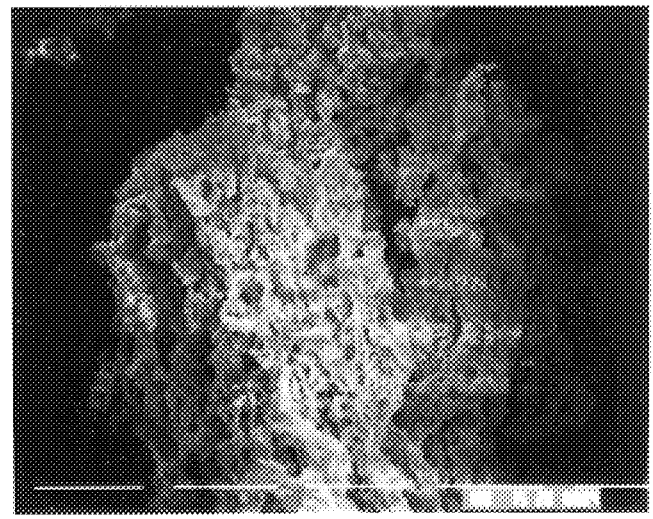
FIG. 5 is an electron microscopic photograph showing the structure of particles of the composition prepared in Example 2 of the present invention, at a magnification of 200 times.
Figure 6:
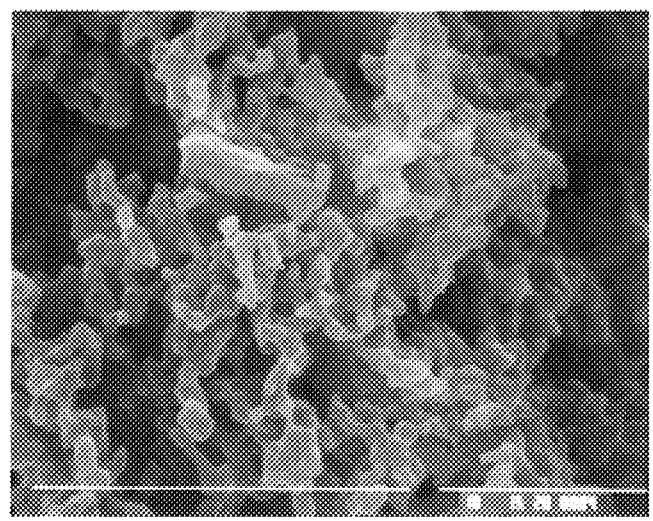
FIG. 6 is an electron microscopic photograph showing the structure of particles of the composition prepared in Example 2 of the present invention, at a magnification of 7500 times.

FIGS. 5 and 6 are electron microscopic photographs of the drug composition obtained in Example 2. The photographs show that the primary particles of sodium hyaluronate are cross-linked and phenytoin is homogeneously present on and between the primary particles.

Obviously, numerous modifications and variations of the present invention are possible in light of the above teachings. It is therefore to be understood that within the scope of the appended claims, the invention may be practiced other than as specifically described herein.

We claim:

1. A drug composition consisting essentially of a drug, which is more soluble in a water-miscible organic solvent than in water, and a mucopolysaccharide in a solid mucopolysaccharide-drug complex, wherein crystals or particles of the drug are disposed about a surface defined by particles of the mucopolysaccharide and wherein the drug in said complex dissolves in water faster than uncomplexed drug alone.

2. The drug composition of claim 1 wherein the crystals or particles of drug are deposited between the particles of mucopolysaccharide.

3. The drug composition of claim 1 wherein the complex is granular.

4. The composition of claim 1 wherein the mucopolysaccharide is chondroitin sulfate, chondroitin, hyaluronic acid, dermatan sulfate, heparin, heparin sulfate, keratan sulfate, keratan polysulfate or is a derivative thereof.

5. A process for producing a drug composition wherein the drug is more in a water-miscible organic solvent than in water, the process comprising the steps of:

(a) providing a solution of said drug dissolved in a water-miscible organic solvent, wherein said solution is free of a polymer additive of polylactic acid, polyglycolic acid, polyhydroxybutyric acid or a coploymer thereof in an amount sufficient to slow the release of the drug from the drug composition produced in step (b) relative to the drug composition produced in step (b) without said polymer additive; and (b) contacting said solution with an aqueous solution of a mucopolysaccharide or a salt thereof thereby to precipitate the drug composition comprising crystals or particles of the drug disposed about a surface defined by particles of the mucopolysaccharide such that the drug in the drug composition dissolves in water faster than the drug alone.

6. A process for producing a drug composition wherein the drug is more soluble in a water-miscible organic solvent than in water, the process comprising the steps of:

(a) contacting an aqueous solution of a mucopolysaccharide with a water miscible organic solvent thereby to produce a mucopolysaccharide precipitate; and (b) contacting the mucopolysaccharide precipitate with a solution of the drug dissolved in the water-miscible organic solvent thereby to produce the drug composition comprising crystals or particles of the drug disposed about a surface defined by particles of the mucopolysaccharide such that the drug in the drug composition dissolves in water faster than the drug alone.

7. The process of claim 5 or 6 wherein the organic solvent is selected from the group consisting of ethanol, 1-propanol, 2-propanol, acetone, N,N-dimethylformamide, formic acid, acetic acid and propionic acid.

8. The process of claim 5 or 6 wherein the concentration of the mucopolysaccharide or salt thereof in the aqueous solution is in the range of from about 0.1 to about 25 percent by weight.

9. The process of claim 5 or 6 wherein the concentration of the drug in the organic solvent solution is in the range of from about 0.01 percent by weight to saturation.

10. The process of claim 5 or 6 wherein the aqueous solution further comprises an inorganic salt.

11. The composition of claim 1 wherein the crystals or particles of the drug are attached to the surface defined by the particles of mucopolysaccharide.

12. A drug composition produced by the method of claim 6.

13. A drug composition produced by the method of claim 6.

14. The process of claim 5 or 6, wherein the mucopolysaccharide is chondroitin sulfate, chondroitin, hyaluronic acid, dermatan sulfate, heparin, heparin sulfate, keratan sulfate, keratan polysulfate or is a derivative thereof.

15. The drug composition of claim 1 wherein the particles of mucopolysaccharide in the complex are crosslinked.

* * * * *

UNITED STATES PATENT AND TRADEMARK OFFICE
CERTIFICATE OF CORRECTION

PATENT NO. : 5,814,621
DATED : September 29, 1998
INVENTOR(S) : Yoshio Kanaya, et al.

It is certified that error appears in the above-identified patent and that said Letters Patent is hereby corrected as shown below:

Column 8, line 46, delete ",".

Column 8, line 48, delete ",".

Signed and Sealed this

Twenty-third Day of March, 1999

Attest:

Q. TODD DICKINSON

*Attesting Officer*  *Acting Commissioner of Patents and Trademarks*